United States Patent
Djurovic

[19]

[11] Patent Number: 5,944,657
[45] Date of Patent: Aug. 31, 1999

[54] RETRACTOR APPARATUS

[76] Inventor: Zarija Djurovic, 370 Devon Ct., Valparaiso, Ind. 46383

[21] Appl. No.: 09/016,900

[22] Filed: Feb. 2, 1998

[51] Int. Cl.[6] ................................................ A61B 17/02
[52] U.S. Cl. .......................................... 600/218; 600/201
[58] Field of Search ................................... 600/201, 204, 600/214, 219, 153, 218; 606/49

[56] References Cited

U.S. PATENT DOCUMENTS

| | | | |
|---|---|---|---|
| 4,043,323 | 8/1977 | Komiya | 600/104 |
| 4,550,240 | 10/1985 | Toida et al. | 600/108 |
| 4,760,840 | 8/1988 | Fournier, Jr. et al. | 600/108 |
| 4,932,952 | 6/1990 | Wojciechowicz, Jr. | 606/49 |
| 5,019,076 | 5/1991 | Yamanashi et al. | 606/49 |
| 5,080,660 | 1/1992 | Buelna | 606/49 |
| 5,318,586 | 6/1994 | Ereren | 600/205 |
| 5,353,784 | 10/1994 | Nady-mohamed | 600/205 |
| 5,447,148 | 9/1995 | Oneda et al. | 600/159 |
| 5,490,819 | 2/1996 | Nicholas et al. | 600/201 |
| 5,554,101 | 9/1996 | Matula et al. | 600/214 |
| 5,667,473 | 9/1997 | Finn et al. | 600/104 |
| 5,702,344 | 12/1990 | Silverstein | 600/104 |
| 5,755,667 | 5/1998 | Schwarteman | 600/219 |

OTHER PUBLICATIONS

FDA Pre Market Notification 510K Device: Laproscopic Surgical Instruments.

*Primary Examiner*—Paul J. Hirsch
*Attorney, Agent, or Firm*—Tilton, Fallon, Lungmus & Chestnut

[57] ABSTRACT

A surgical retracting device includes a body, at least one pivotable finger, and an actuating assembly that moves the finger between open and closed positions. The body defines a passageway and openings that allow suctioning and irrigating through the device. In addition, the device includes a cauterizing assembly for cauterizing tissue of a patient.

38 Claims, 4 Drawing Sheets

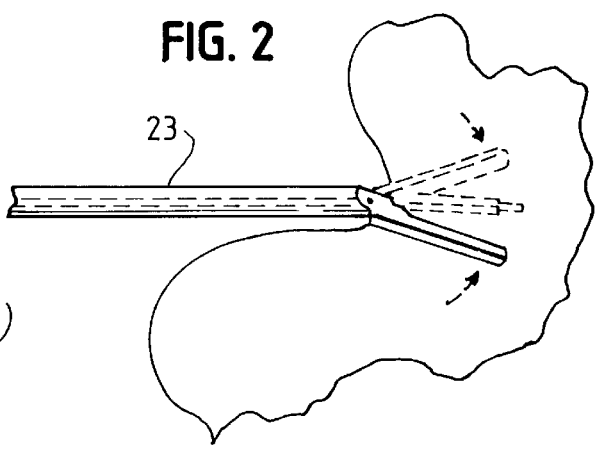
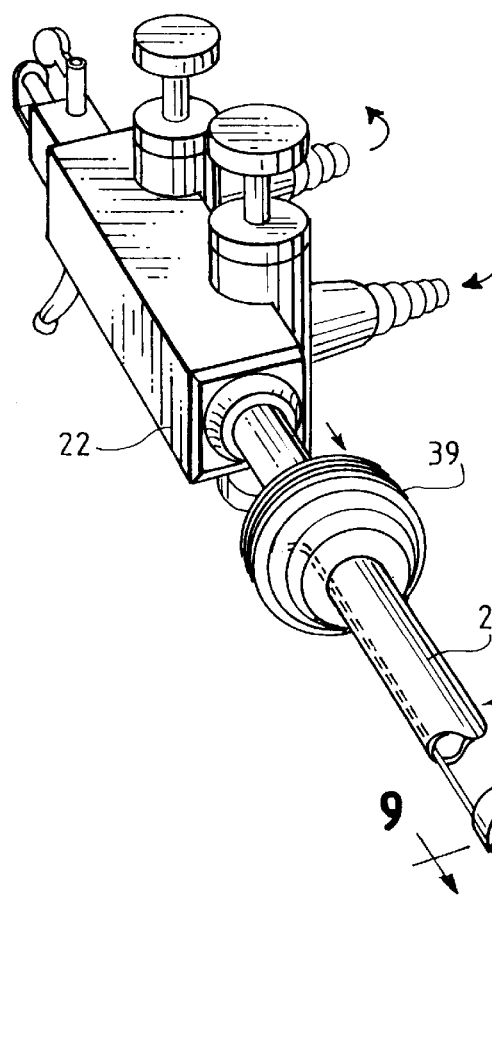
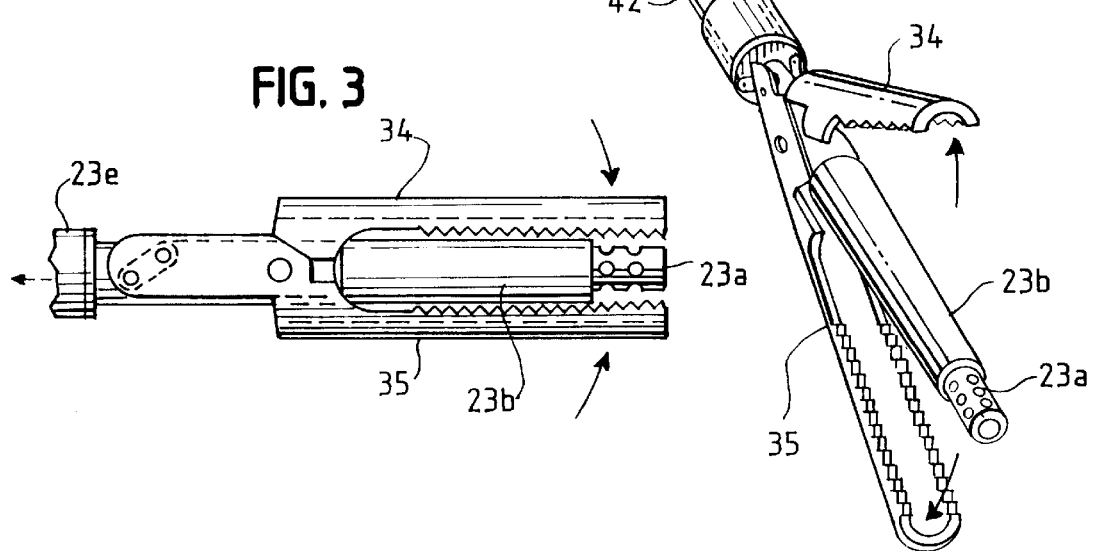

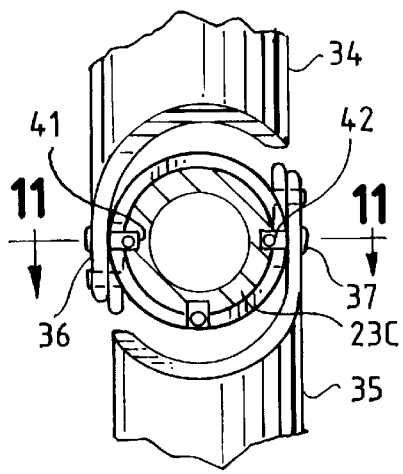
FIG. 10
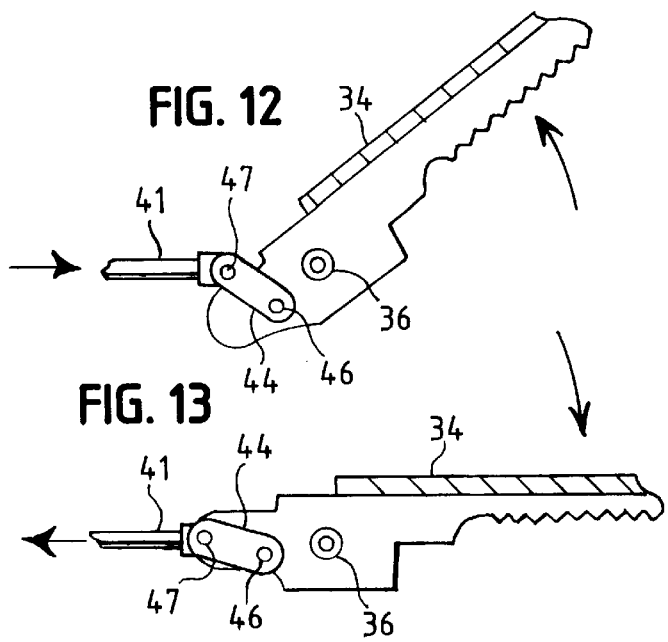
FIG. 12
FIG. 13
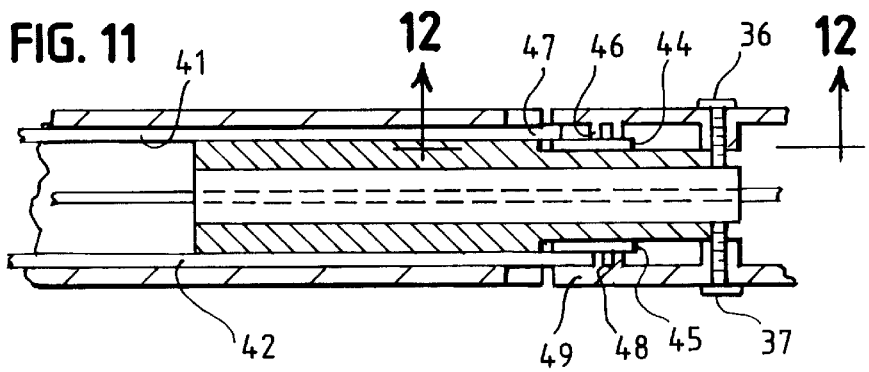
FIG. 11
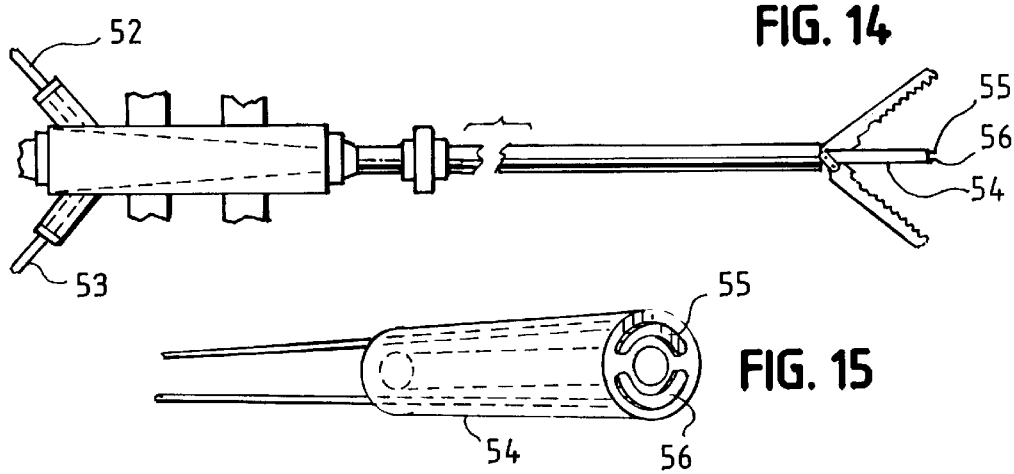
FIG. 14
FIG. 15

RETRACTOR APPARATUS

BACKGROUND OF THE INVENTION

1. Field Of The Invention

The present invention relates to a surgical retracting device and more particularly to a multi-functional surgical device with which a surgeon may perform retracting, clamping, irrigating, suctioning and cauterizing procedures. Although the device of the present invention finds particular relativity in laproscopic procedures, it may also provide one or more of the functions outlined above in other surgical procedures.

2. Description Of The Prior Art

Surgical procedures typically require the use of a large number of implements and devices. For example, a surgeon may use separate instruments for grasping, retracting, suctioning, irrigating, and cauterizing in one operation. The use of such a large number of instruments unduly complicates operations and extends their duration.

The prior art includes a wide variety of instruments that perform the functions identified above. However, each one of these devices performs one or two of the functions.

A reduction in the number of instruments would reduce the duration and complexity of an operation. The retraction apparatus of the present invention does just that. It performs retracting, grasping, suctioning, irrigating and electro-cauterization functions effectively and reliably. It is a simple device, considering all the functions it performs; and it minimizes the cost of manufacture and assembly.

SUMMARY OF THE INVENTION

In accordance with one embodiment of the present invention, a retractor apparatus includes a body with a first end and a second end. It also includes one or more fingers pivotally mounted to the body at the first end and an actuating assembly that drives the fingers between open and closed positions. The actuating assembly comprises an actuating member slidably mounted to the body and linkage means for connecting the fingers and the actuating member.

A passageway that extends through the body from the first end to the second end communicates with the outside of the body through hole and openings at the two ends. (Valve means normally close the various openings at the second end.) This passageway facilitates suctioning and irrigating. It also provides an entryway into a patient for other instruments such as small diameter optical devices.

An electro-cauterization assembly of the apparatus of the present invention allows a surgeon to cauterize a wound with the apparatus. This assembly includes at least one wire that extends across the body and an electrical contact at the first end of the body. The wire engages the contact which a surgeon places proximate tissue of a patient; and the contact cauterizes the tissue.

BRIEF DESCRIPTION OF THE DRAWINGS

For a more complete understanding of this invention, one should now refer to the embodiment illustrated in greater detail in the accompanying drawings and described below by way of an example of the invention. In the drawings:

FIG. 1 is a perspective view of the retractor apparatus of the present invention with a portion cut away to show an internal linkage assembly;

FIG. 2 is a partial perspective view of a first end of the apparatus shown in FIG. 1, showing a pair of pivotable fingers;

FIG. 3 is a partial side elevation view of the pivotable fingers of the retractor apparatus of FIG. 1;

FIG. 10 is a sectional view taken along line 10—10 in FIG. 4;

FIG. 11 is a sectional view taken along line 11—11 in FIG. 4;

FIG. 12 is a sectional view taken along line 12—12 in FIG. 11, showing a finger in an open portion;

FIG. 13 is the sectional view of FIG. 12, showing the finger of the apparatus in a closed position;

FIG. 14 is a plan view of a modification of the retractor apparatus of the present invention, incorporating a bi-polar cauterization assembly; and FIG. 15 is a partial perspective view of the contacts of the cauterization assembly disposed at the first end of the apparatus.

Figure 4:
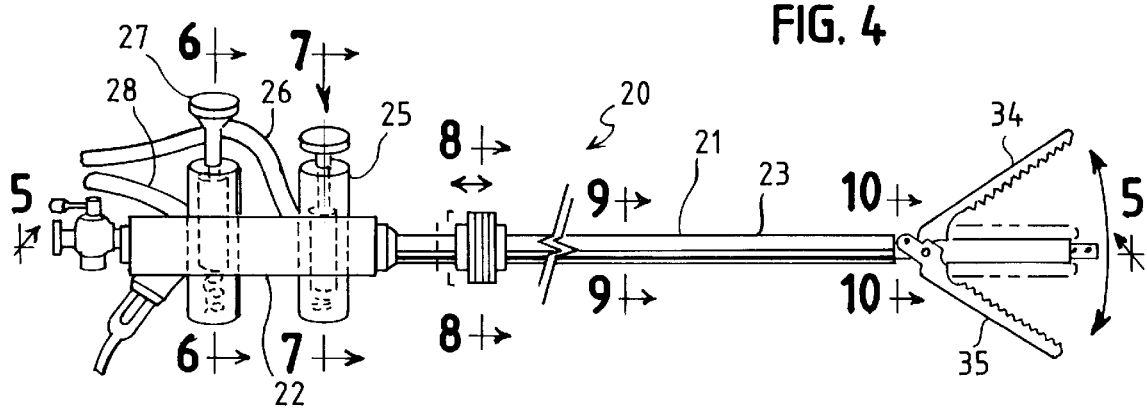
FIG. 4 is a side elevation view of the retractor apparatus.

While the following disclosure describes the invention in connection with one embodiment and a modification of that embodiment, one should understand that the invention is not limited to this embodiment and modification. Furthermore, one should understand that the drawings are not to scale and that graphic symbols, diagrammatic representatives, and fragmentary views, in part, illustrate the embodiment. In certain instances, the disclosure may not include details which are not necessary for an understanding of the present invention such as conventional details of fabrication and assembly.

DETAILED DESCRIPTION OF THE DRAWINGS

Turning now to the drawings and referring specifically to FIGS. 1–5, the retractor assembly of the present invention shown generally at 20 includes a body 21 with a block segment 22 and a tube segment 23 secured at one end to the block segment 22 (by press fitting or other similar procedures). The other, free end of the tube segment 23 defines the front end or the first end of the body 21, while the block segment 22 lies at the back end or the second end of the body. These components, as well as those described below are made of stainless steel, medical plastic (e.g., ULTEM) or any other suitable sterilizable material of high strength and rigidity.

A bore 22a that extends through the block segment 22 and a central bore 23a through the tube segment 23 form an elongate and generally round passageway 24 longitudinally of the body 21, from the first end of the body 21 and apparatus 20 to the second end of the body 21 and apparatus 20. This passageway 24 contains various components described below; and it directs irrigating fluids into a site in a patient, allows suctioning of the site, and serves as a conduit for other smaller devices, such as optical instruments into a patient's body.

Figure 6:
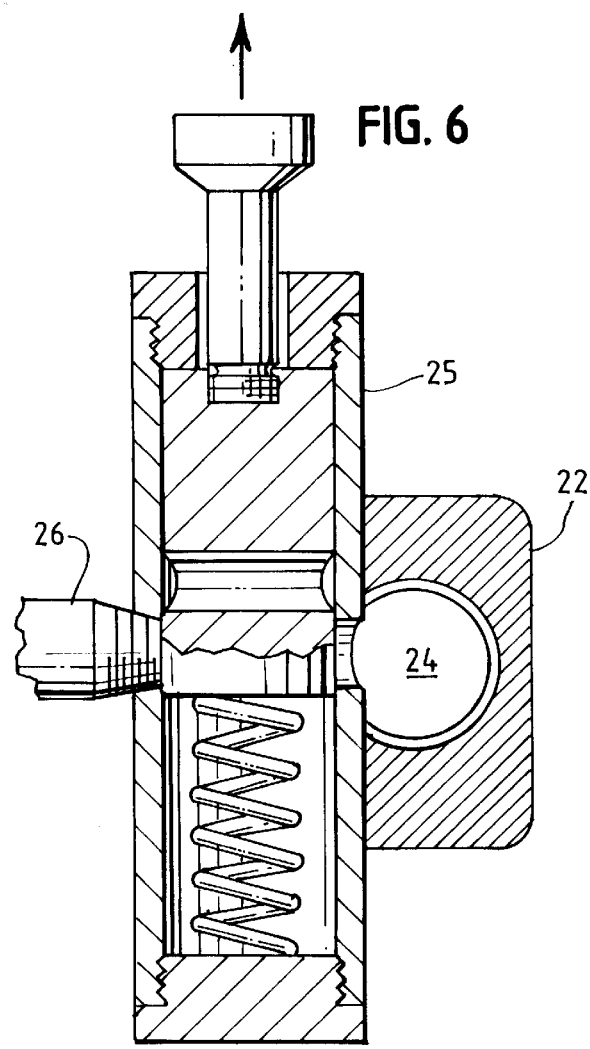
FIG. 6 is a sectional view taken along line 6—6 in FIG. 4.
Figure 7:
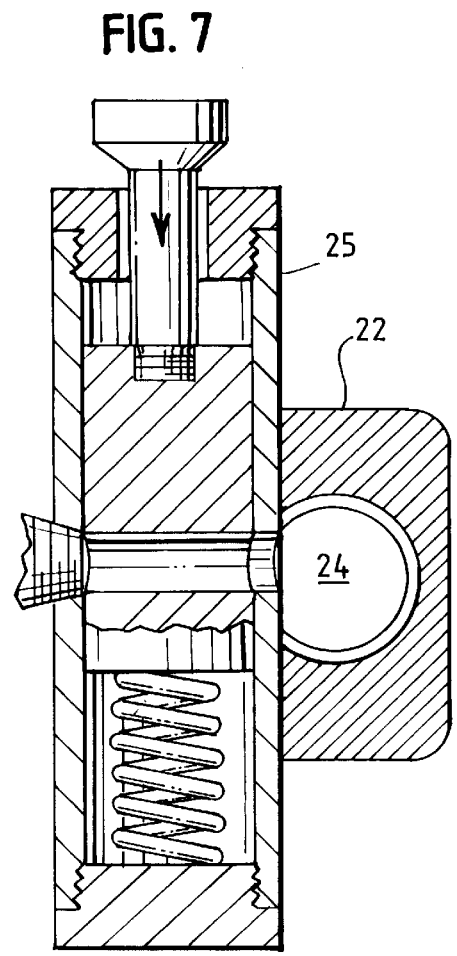
FIG. 7 is a sectional view taken along line 7—7 in FIG. 4.
Figure 8:
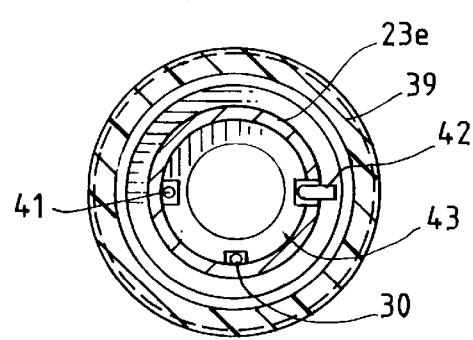
FIG. 8 is a sectional view taken along line 8—8 in FIG. 4.
Figure 9:
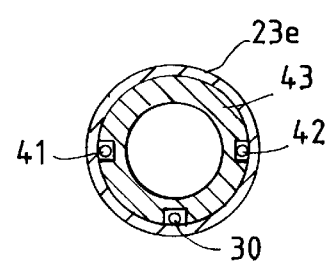
FIG. 9 is a sectional view taken along line 9—9 in FIG. 4.

The block segment 22 serves as a handle and defines a first opening 22b that communicates with the passageway 24. A conventional trumpet valve 25 secured to the block segment 22 normally closes this opening 22b and controls the discharge (into the passageway 24) of irrigating fluid or other material provided by a conduit 26 (see FIGS. 6 and 7). Similarly, the block segment 22 also defines a second opening 22c that communicates with the passageway 24; and a trumpet valve 27 (supported by the block segment 22) normally closes this opening 22c and controls the discharge (from the passageway 24) of materials such as fluids and solids into a conduit 28.

Although the embodiment shown in the drawings has trumpet valves for the openings 22b and 22c, other suitable valves may serve as replacements. In addition, the block segment 22 may define more openings along the side that includes the openings 22b and 22c; or any other side of the block segment and the apparatus 20 may include additional valves to close those additional openings. The additional openings would allow simultaneous connection with other utilities that may pass through the passageway 24 of the retractor apparatus 20.

The block segment 22 further defines openings comprising the ends of the bore 22a, including a third opening 22d closed by a valve 29 and a fourth opening 22e that receives the tube segment 23. The valve 29 allows the passage of small diameter instruments such as conventional, miniature optical instruments and other similarly sized instruments to extend into the passageway 24 and move out of the other end of the passageway 24 and the apparatus 20. Yet another opening 22f in the block segment 22 allows a wire 30 of a mono-polar electro-cauterizing assembly 31 to extend into the body 21.

Figure 5:
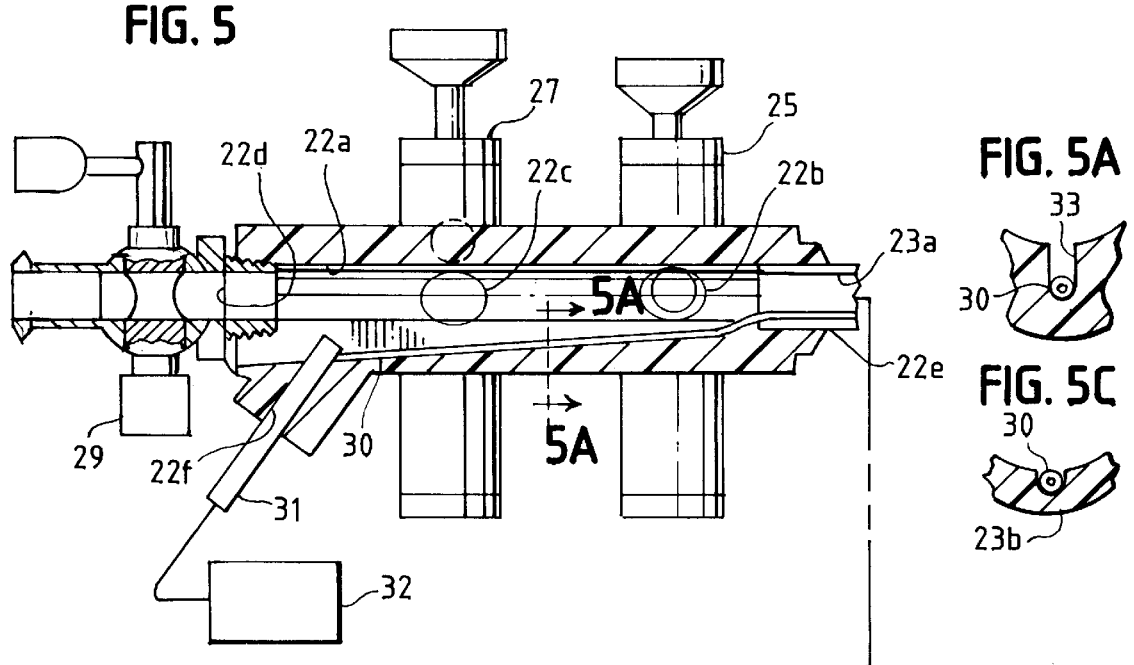
FIG. 5 is a sectional view taken along line 5—5 in FIG. 4.
Figure 5A:
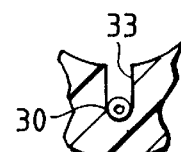
FIG. 5A is a sectional view taken along line 5A—5A in FIG. 5.

The wire 30 extends from a power and control module 32, through the opening 22f, and into a trough 33 that lies below the passageway 24 and communicates with the passageway 24 as shown in FIGS. 5 and 5A. The wire 30 extends through the trough 33 and then into and along the passageway 24 to the first end of the body 21 where it energizes a contact comprising and end tube section 23a made of metal and forming the distal end of the tube segment 23. (Insulation covers the wire 30 until it engages the end tube section 23a).

Figure 5C:
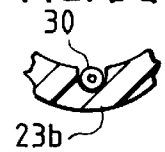
FIG. 5C is a sectional view taken along line 5C—5C in FIG. 5B.
Figure 5B:
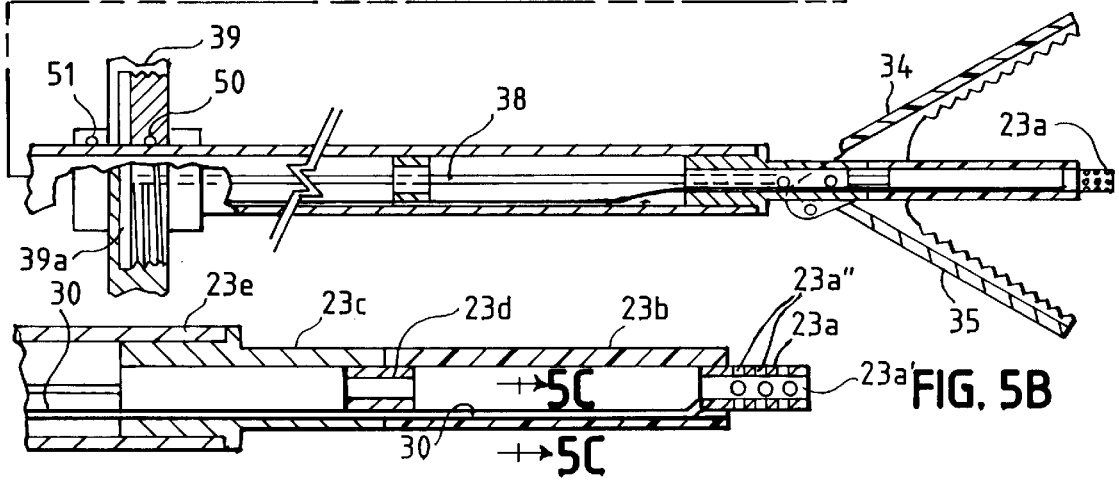
FIG. 5B is a partial and enlarged sectional view of the right or first end portion of the apparatus.

In addition to the tube section 23a, the tube segment 23 includes an outer tube section 23b that receives the end tube section 23a at one end; an outer tube section 23c disposed in end-to-end relation with the outer tube section 23b; an inner tube section 23d that extends into the outer sections 23b and 23c and connects the two outer sections together; and a main tube section 23e that receives an end portion of the outer tube section 23c. (See FIGS. 5 and 5B). The various tube sections lie in the arrangement shown in FIG. 5B secured together by epoxy. In the embodiment shown, the sections 23a, 23c, 23d, and 23e are made of stainless steel while section 23b is made of plastic. In addition, the sections 23c and 23b define a groove through which the wire 30 extends (See FIG. 5C).

The end tube section 23a defines a hole 23a' which is the main opening to the passageway 24 at the first end of the body 21. It also defines a plurality of secondary holes 23a" disposed inwardly of the hole 23a'. The secondary holes 23a" allow a vacuum pump (not shown) connected to the conduit 26 to continue the suctioning of a site in a patient after tissue or other materials block the hole 23a'. Similarly, the secondary holes 23a" allow the apparatus 20 to irrigate a site when the primary hole 23a' closes.

A pair of fingers 34 and 35 pivotally mounted to the outer tube section 23c, as at 36 nd 37, respectively, (see FIGS. 10–13) and an actuating assembly 38 (see FIGS. 1 and 5) allow an operator to easily retract or grasp an object with the apparatus 20. The fingers pivot between a closed position shown in FIG. 3 and an open position shown in FIG. 1. They grasp organs and other material against the outer tube section 23b. And, although the embodiment shown in the drawings includes two stainless steel fingers, the apparatus 20 may alternatively have only one finger or more than two.

The actuating assembly 38 that drives the fingers 34 and 35 between the open and closed positions includes an actuating member 39 slidably mounted to the main tube section 23e of the tube segment 23. It also includes a linkage assembly 40 with rods 41 and 42, a bushing 43, and pivot elements 44 and 45. Suitable pivot connections secure one end of the pivot element 44 to the finger 34 (as at 46) and the opposite end to the front end of the rod 41 (as at 47). The rod 41 extends past the outer tube section 23c, in sliding relation with that section 23c (as shown in FIGS. 10). The back end of the rod 41 lies fixedly secured to the bushing 43.

Similarly, pivot connections secure one end of the pivot element 45 to the finger 35 (as at 48) and the opposite end to the front end of the rod 42 (as at 49). The rod 42 extends past the outer tube section 23c, in sliding relation with that section 23c. It also extends past the bushing 43 and lies fixedly secured to the bushing 43. Its back end extends outwardly of the main tube section 23e through a slot (not shown) in the main tube section and into a pocket 39a of the actuating member 39. (See FIG. 5) it pair of resilient O-rings 50 and 51 in the actuating member 39 seal the slot from the outside of the apparatus 20. The ends of the slot serve as stops for the actuating member 39, stops which also help define the limits of the pivoting motion for the fingers 34 and 35.

FIGS. 14 and 15 show a modification of the apparatus 20. In this alternative, the electro-cauterizing assembly 32 is a conventional bi-polar device with a negative lead wire 52 and a positive lead wire 53. The contact at the first end of the apparatus 20 includes a non-conductive end tube section 54 with conductive contacts 55 and 56 connected to the wires 52 and 53, respectively. (See FIG. 15). This alternative provides a second conductive path through the apparatus 20 rather than between the control unit (not shown) and the patient as it would in the arrangement described above.

While in the above description and the drawings disclose and illustrate one embodiment and a modification, one should understand, of course, that the invention is not limited to this embodiment and modification. Those skilled in the art to which the invention pertains may make other modifications and other embodiments employing the principles of this invention, particularly upon considering the foregoing teachings. Therefore, by the appended claims, the applicant intends to cover any modifications and other embodiments as incorporate those features which constitute the essential features of this invention.

What is claimed is:

1. A retractor apparatus comprising: an elongate body with a first end and a second end; at least one finger pivotally mounted to the body at the first end; an actuating member slidably mounted to the body at the second end for sliding movement longitudinally of the body between first and second predetermined limits; linkage means for connecting the finger and the actuating member; said actuating member and said linkage means cooperating to drive the finger between a closed position and an open position.

2. The retractor apparatus of claim 1, wherein a second finger lies pivotally mounted to the body at the first end of the body opposite the one finger, the linkage means connecting the second finger to the actuating member.

3. The retractor apparatus of claim 2, wherein the body includes an end portion that extends between the first and second fingers, said end portion and said fingers being substantially co-extensive when the fingers lie in the closed position.

4. The retractor of claim 1, wherein the body defines a passageway that extends from the first end to the second end of the body and communicates with the outside of the body through a hole at the first end.

5. The retractor apparatus of claim 4, wherein the passageway communicates with a plurality of holes at the first end.

6. The retractor apparatus of claim 4, wherein the body defines a first opening at the second end in communication with the passageway, and a first valve means lies mounted to the body for normally closing said first opening.

7. The retractor apparatus of claim 6, wherein the body defines a second opening at the second end in communication with the passageway, and a second valve means lies mounted to the body for normally closing said second opening.

8. The retractor apparatus of claim 7, wherein the body defines a third opening at the second end in communication with the passageway, and a third valve means lies mounted to the body for normally closing said third opening.

9. The retractor apparatus of claim 1, further comprising cauterizing means mounted to said body for cauterizing tissue of a patient, said cauterizing means including contact means disposed at the first end of the body for approaching tissue of a patient and cauterizing the tissue.

10. The retractor apparatus of claim 4, wherein the body includes a block segment at the second end of the body and a tube segment that lies secured to the block segment and extends outwardly of the block segment.

11. The retractor apparatus of claim 10, wherein the passageway includes a central bore of the tube segment and co-axial bore in the block segment.

12. A retractor apparatus comprising: an elongate body with a first and second end; at least one finger pivotally mounted to the body at the first end; actuating means mounted to the body for driving the finger to and from closed and open positions; and cauterizing means mounted to the body for cauterizing tissue of a patient, said cauterizing means including contact means disposed at the first end of the body for approaching tissue of a patient and cauterizing the tissue.

13. The retractor apparatus of claim 12, wherein a second finger lies pivotally mounted to the body at the first end of the body opposite the one finger, the linkage means connecting the second finger to the actuating member.

14. The retractor apparatus of claim 12, wherein the body includes an end portion that extends between the first and second fingers, said end portion and said fingers being substantially co-extensive when the fingers lie in the closed position.

15. The retractor of claim 12, wherein the body defines a passageway that extends from the first end to the second end of the body and communicates with the outside of the body through a hole at the first end.

16. The retractor apparatus of claim 15, wherein the passageway communicates with a plurality of holes at the first end.

17. The retractor apparatus of claim 15, wherein the body defines a first opening at the second end in communication with the passageway, and a first valve means lies mounted to the body for normally closing said first opening.

18. The retractor apparatus of claim 17, wherein the body defines a second opening at the second end in communication with the passageway, and a second valve means lies mounted to the body for normally closing said second opening.

19. The retractor apparatus of claim 18, wherein the body defines a third opening at the second end in communication with the passageway, and et third valve means lies mounted to the body for normally closing said third opening.

20. The retractor apparatus of claim 15, wherein the body includes a block segment at the second end of the body and a tube segment that lies secured to the block segment and extends outwardly of the block segment.

21. The retractor apparatus of claim 20, wherein the passageway includes a central bore of the tube segment and coaxial boar in the block segment.

22. A retractor apparatus comprising: an elongate body with a first end and a second end; at least one finger pivotally mounted to the body at the first end; and actuating means mounted to the body for driving the finger to and from closed and open positions; the body defining a passageway that extends from the first end to the second end and communicates with the outside of the body through a hole at the first end; the body defining a first opening at the second end in communication with the passageway; a first valve means mounted to the body for normally closing said first opening said first opening, hole, and passageway extending generally along a straight line.

23. The retractor apparatus of claim 22, wherein a second finger lies pivotally mounted to the body at the first end of the body opposite the one finger, the linkage means connecting the second finger to the actuating member.

24. The retractor apparatus of claim 22, wherein the body includes an end portion that extends between the first and second fingers, said end portion and said fingers being substantially co-extensive when the fingers lie in the closed position.

25. The retractor apparatus of claim 22, wherein the passageway communicates with a plurality of holes at the first end.

26. The retractor apparatus of claim 22, wherein the body defines a second opening at the second end in communication with the passageway, and a second valve means lies mounted to the body for normally closing said second opening.

27. The retractor apparatus of claim 26, wherein the body defines a third opening at the second end in communication with the passageway, and a third valve means lies mounted to the body for normally closing said third opening.

28. The retractor apparatus of claim 22, further comprising cauterizing means mounted to said body for cauterizing tissue of a patient, said cauterizing means including contact means disposed at the first end of the body for approaching tissue of a patient and cauterizing the tissue.

29. The retractor apparatus of claim 22, wherein the body includes a block segment at the second end of the body and a tube segment that lies secured to the block segment and extends outwardly of the block segment.

30. The retractor apparatus of claim 22, wherein the passageway includes a central bore of the tube segment and coaxial bore in the block segment.

31. A retractor apparatus comprising: a rigid, elongate body with a first end and a second end, said body defining a passageway from the first end to the second end, said passageway being generally straight and open to at least one finger member pivotally mounted to the body at the first end; an actuator mounted to the body for movement between predetermined limits; and a linkage, including a rigid rod for connecting the actuator and the finger; the actuator and linkage driving the finger between open and closed positions; the passageway communicating with the outside of the body at the second end through a first opening, a closing member normally closing the first opening; the passageway and the first opening extending generally longitudinally of the body and along a straight line.

32. The retractor apparatus of claim 31, wherein a second finger lies pivotally mounted to the body at the first end of the body opposite the one finger, the linkage connecting the second finger to the actuator.

33. The retractor apparatus of claim 31, wherein the body includes an end portion that extends between the first and second fingers, said end portion and said fingers being substantially co-extensive when the fingers lie in the closed position.

34. The retractor apparatus of claim 31, wherein the passageway communicates with a plurality of holes at the first end.

35. The retractor apparatus of claim 31, wherein the body defines a second opening at the second end in communication with the passageway, and a second valve means lies mounted to the body for normally closing said second opening.

36. The retractor apparatus of claim 35, wherein the body defines a third opening at the second end in communication with the passageway, and a third valve means lies mounted to the body for normally closing said third opening.

37. The retractor apparatus of claim 31, further comprising cauterizing means mounted to said body for cauterizing tissue of a patient, said cauterizing means including contact means disposed at the first end of the body for approaching tissue of a patient and cauterizing the tissue.

38. The retractor apparatus of claim 31, wherein the actuator lies slidably mounted to the body for sliding movement longitudinally of the body.

* * * * *